United States Patent [19]

McAlister et al.

[11] Patent Number: 4,703,763

[45] Date of Patent: Nov. 3, 1987

[54] BLOOD SAMPLE SYRINGE

[75] Inventors: Gary B. McAlister, Beacon Falls; James Malloy, Wilton, both of Conn.

[73] Assignee: Sherwood Medical Company, St. Louis, Mo.

[21] Appl. No.: 745,855

[22] Filed: Jun. 17, 1985

[51] Int. Cl.$^4$ .............................................. A61B 5/00
[52] U.S. Cl. ..................................... 128/765; 604/190
[58] Field of Search ....................... 128/760, 762–767, 128/771; 604/190, 222, 405–406

[56] References Cited

U.S. PATENT DOCUMENTS

| | | |
|---|---|---|
| 3,075,525 | 1/1967 | McConnaughey . |
| 3,901,402 | 8/1975 | Ayres . |
| 3,941,129 | 3/1976 | Pleznac . |
| 3,960,139 | 6/1976 | Bailey . |
| 3,978,846 | 9/1976 | Bailey . |
| 3,985,122 | 10/1976 | Topham . |
| 4,020,831 | 5/1977 | Adler . |
| 4,036,232 | 7/1977 | Genese . |
| 4,133,304 | 1/1979 | Bailey . |
| 4,206,768 | 6/1980 | Bailey ................................. 128/763 |
| 4,257,426 | 3/1981 | Bailey . |
| 4,299,238 | 11/1981 | Baidwan ............................. 128/763 |
| 4,323,066 | 4/1982 | Bourdon . |
| 4,326,540 | 4/1982 | Bailey ................................. 128/763 |
| 4,327,745 | 5/1982 | Ford ................................... 128/765 |
| 4,340,067 | 7/1982 | Rattenborg ......................... 128/763 |
| 4,361,155 | 11/1982 | Anastasio ...................... 128/765 X |
| 4,373,535 | 2/1983 | Martell ............................... 128/765 |
| 4,424,817 | 1/1984 | Williams ............................. 128/766 |
| 4,439,187 | 3/1984 | Butterfield ......................... 604/111 |
| 4,447,229 | 8/1983 | Butterfield ......................... 604/111 |
| 4,448,206 | 5/1984 | Martell ............................... 128/765 |
| 4,466,446 | 8/1984 | Baidwan et al. .................... 128/765 |
| 4,469,482 | 9/1984 | Lissenburg et al. ............ 128/765 X |
| 4,507,117 | 3/1985 | Vining et al. ...................... 604/196 |

FOREIGN PATENT DOCUMENTS

WO81/03426 12/1981 PCT Int'l Appl. .

Primary Examiner—William E. Kamm
Assistant Examiner—Angela D. Sykes
Attorney, Agent, or Firm—Brumbaugh, Graves, Donohue & Raymond

[57] ABSTRACT

A blood sampling syringe is provided with a plug element at a selected position in a syringe barrel thereby defining a pre-set sample volume. A plunger element is provided on the side of the plug element away from the syringe neck to enable aspiration of a pre-set volume of blood sample. The plug element is provided with an air permeable, fluid impermeable sealing member, and in a preferred embodiment seals after fluid has entered the sealing member.

4 Claims, 1 Drawing Figure

U.S. Patent  Nov. 3, 1987  4,703,763
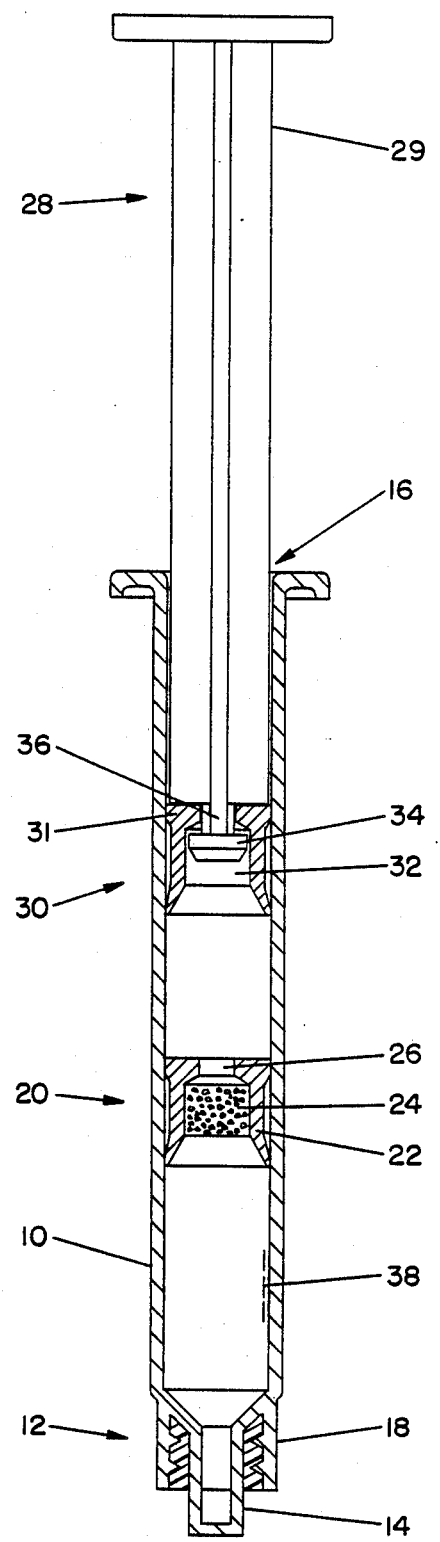

BLOOD SAMPLE SYRINGE

BACKGROUND OF THE INVENTION

The present invention relates to a novel arterial blood sample syringe for use in connection with blood gas analysis. More specifically, the syringe of the present invention is designed to substantially reduce or eliminate error in blood sampling procedures through the use of a preset means that defines the maximum volume of blood that can be delivered to the syringe either by aspiration or by arterial blood pressure. Further, the syringe of the present invention provides improvement in elimination of air contamination in connection with obtaining an arterial blood sample.

Earlier U.S. Pat. No. 4,133,304 discloses an apparatus for obtaining a fixed volume blood sample, which includes a sample gathering capillary tube which is vented by the use of a fibrous thread, which can be removed to seal the capillary tube. The earlier device in one embodiment provides an arrangement for blood aspiration through the use of a piston which surrounds the capillary tube.

The prior art device has a rather complex construction and is difficult to use in connection with some blood-gas analyzing equipment which require that a blood sample be ejected into the analyzing equipment.

Accordingly, it is an object of the present invention to provide a preset fixed maximum volume blood sampling syringe which can be used in either the self-venting mode, wherein a sample is obtained by arterial blood pressure, or in an aspiration mode, wherein blood is drawn by vacuum suction. It is another object of the invention to provide such device which is simple to manufacture and which is capable of easily expelling a blood sample into blood-gas analyzing equipment.

SUMMARY OF INVENTION

According to the present invention, there is provided a hypodermic syringe, the barrel of which contains a pre-set plug element which precisely defines the volume of a blood sample to be obtained. The plug element is arranged to be air-permeable but fluid impermeable, so that fluid entering the syringe will fill the space between the plug and the needle as air flows out through the plug, and fluid flow stops upon wetting of the plug. The syringe further includes a slideable plunger and rod assembly located between the plug and the open end of the barrel. The plunger can be used to draw air through the plug element to form a partial vacuum and thereby aspirate fluid into the barrel. After a sample has been taken the plunger can be used to expel a sample through the needle end of the syringe. The plunger and rod assembly preferably form at the point of connection a valve which permits outward air flow past the plunger, but closes to prevent inward air flow when aspirating.

In a preferred embodiment of the invention the air permeable, fluid impermeable plug element has a sealing member formed of a material arranged to allow penetration of fluid into the material prior to sealing and thereby trap a small volume of fluid, such as blood in the sealing material. The material may comprise a self-sealing porous polyethylene with a pore size which allows entry of fluid and which seals the pores upon entry of the fluid.

In accordance with the invention there is provided a method for drawing a fixed maximum volume blood sample by aspiration using the inventive device.

BRIEF DESCRIPTION OF THE DRAWING

The FIGURE is a longitudinal sectioned view of a syringe constructed in accordance with a preferred embodiment of the present invention.

DESCRIPTION OF THE PREFERRED EMBODIMENT

The drawing shows a cross-sectional view of a syringe assembly in accordance with the present invention. The syringe assembly uses a conventional cylindrical syringe barrel 10 which has a first open end 16 and a second end 12 adapted to receive either a hyperdermic needle or a cap, which is not shown. For this purpose, end 12 has a neck 14 for receiving a hyperdermic needle, and in the illustrated embodiment also includes a Luer lock arrangement 18 for securing attachment of a needle or plug to neck 14.

A plug element 20 is arranged at a fixed position within barrel 10. The position of plug element 20 defines a blood sample volume consisting of the interior space of barrel 10 between plug element 20 and neck 14.

Plug element 20 has an exterior member 22 made of Kraton. Member 22 is formed to resiliently engage the interior of barrel 10 to form a seal between barrel 10 and member 22. Interior passage 26 is formed to extend longitudinally through the center of plug element 20. Sealing member 24 is held firmly within an enlarged section of longitudinal passage 26 of member 22.

Sealing member 24 is arranged to pass air through the center of plug 20 but to seal and prevent passage of fluid such as blood. The particular sealing member 20 used in the embodiment shown in the drawing is of special design and arranged to allow blood to penetrate the sealing member to a partial thickness of the member prior to sealing. This arrangement of sealing member 24 provides for relatively complete elimination of air in the sample volume between plug element 20 and neck 14 when blood enters the syringe either by arterial blood pressure or aspiration, as will be further explained.

A suitable material for plug element 24 is self-sealing porous polyethylene with a relatively large pore size which enables fluid to enter the sealing member 24. The self-sealing porous plastic material is dissolved in the water of a fluid, such as blood, and upon dissolving causes a thickening of the fluid in the interior of sealing member 24 which prevents further flow of blood through the entire thickness of member 24, thereby blocking passage 26. A suitable material for member 24 can be obtained from Porex Technologies of Fairburn, Ga. and has a designation 1324.

The syringe assembly shown in the drawing further includes a plunger 28 having a plunger rod 29 and a piston member 30. Piston 30 includes cylindrical member 31, also made of Kraton and also in sealing engagement around its periphery with the interior of barrel 10. Member 31 includes a longitudinal interior air channel 32. A valve member 34 is arranged within air channel 32 and connected to plunger rod 29 by a non-circular connecting member 36. Accordingly, in the relaxed condition illustrated air can freely flow through piston 30. When plunger rod 29 is drawn outwardly from syringe barrel 10, valve member 34 engages a shoulder on cylindrical member 31 and seals the air channel 32 so that air can no longer enter barrel 10 and a partial vacuum occurs within barrel 10.

The interior of barrel 10, particularly in the sample chamber between plug element 20 and neck 14 is advantageously provided with Heparin coating 38 to prevent blood clotting when a sample is within the sample volume.

When supplied to a technician or nurse who is to obtain a blood sample, the syringe shown in the drawing has plug element 20 at a pre-set position within barrel 10 which defines the volume of blood sample to be obtained. Plunger 28 is at a position where piston 30 is spaced between plug element 20 and opened end 16 of barrel 10. It is important that the technician be instructed not to move plunger 28 into barrel 10 in a manner which would disturb the pre-set position of plug element 20. A temporary mechanical stop may be provided to reinforce this instruction.

In order to obtain an arterial blood sample, for example for blood gas analysis, a needle is attached to neck 14 and inserted into the patient's artery. For a normal adult patient, with adequate blood pressure, arterial blood pressure is usually sufficient to cause blood to flow into barrel 10 through neck 14. As blood enters, it contacts and becomes mixed with the Heparin coating 38. During the blood collecting process, plug element 20 should be elevated with respect to neck 14 so that air in the sample chamber between element 20 and neck 14 can flow through sealing member 24 and air passage 26 of plug element 20 and also through air channel 32 past valve 34 in piston member 31.

When the level of the blood sample reaches sealing member 24, air within the sample chamber is driven out as the blood enters the sealing member 24. Following partial penetration, for example, approximately 25% of the distance through sealing member 24, the sealant material comprising the sealing member 24 causes a thickening of the blood and sealing of the porous passageways, thereby preventing further flow of blood past plug element 20.

Having obtained a blood sample, the technician may remove the needle from the patient's artery and can thereafter use plunger 28 to move plug element 20 toward neck 14 to expel the blood sample through neck 14 into a blood gas analyzer.

It should be noted that during the sampling process, contact between the blood sample and air has been carefully minimized, since air is quickly driven through sealing member 24 and the portion of the blood sample that has contacted air enters sealing member 24 and is trapped therein. The portion of the blood sample injected into the analyzing device has not had contact with air and contains no remnant air bubbles, which might arise in a conventional syringe where there is an air space within neck 14 and the funnel portion of barrel 10 prior to obtaining a sample.

In a second mode of operation, the syringe shown in the drawing can be used to aspirate a blood sample from a patient with inadequate arterial blood pressure. For this purpose a needle is attached to neck 14 and inserted into an artery as in the self-venting operation. In order to draw a blood sample under partial vacuum into syringe barrel 10, plunger 28 is drawn outwardly from syringe barrel 10 causing valve 34 to close air passage 32 within piston 30 and generating a partial vacuum within syringe barrel 10 on the side of piston 30 facing barrel end 12. Because piston 30 starts at a location part-way down barrel 10, a rather gentle vacuum is generated, which is sufficient for drawing the blood sample, but does not cause extraction of gases from the blood sample nor does it cause hemolysis of red blood cells. In the aspiration operation, air is drawn through sealing member 24 thereby eliminating presence of air within the sample chamber once the blood level reaches and enters sealing member 24.

An important advantage of the present invention is the ability of the devices, as described, to provide for a fixed maximum volume of blood sample, determined by the preset position of plug element 20, even when the device is used in the aspiration mode. Unlike prior arrangements, plug element 20 does not move within barrel 10 when blood is aspirated using the syringe.

Another important advantage of the invention is that it enables almost total elimination of air within the sample volume. The arrangement illustrated enables natural flow of air, in either the self-venting mode or the aspiration mode, through sealing member 20 until the blood sample actually enters and penetrates the sealing member pushing trapped air bubbles well into the sealing member. Another advantage of the invention is the fact that neither plug element 20 nor piston 30 move into the portion of barrel 10 containing the blood sample until plunger 28 is used to expel the blood sample for analysis. Accordingly, the Heparin coating 38 on the interior of barrel 10 is not disturbed by the passage of a piston element.

While there has been described what is believed to be the preferred embodiment of the present invention, those skilled in the art will recognize that other changes and modifications may be made thereto without departing from the spirit of the invention, and it is intended to claim all such changes and modifications as fall within the true scope of the invention.

I claim:

1. A syringe assembly for obtaining a fixed maximum volume liquid sample, comprising:

a cylindrical syringe barrel open at a first end and adapted to receive a hypodermic needle at a second end;

a cylindrical plug element comprising a resilient member arranged at a selected longitudinal position in said syringe barrel defining said fixed maximum volume for said sample as the interior volume of said barrel between said second end and said plug element, said plug element being arranged entirely within said barrel to prevent manual increase in said fixed volume, and being arranged to permit flow of air therethrough and to prevent flow of liquid therethrough, and said plug element forming an air and liquid seal against the inside of said barrel and having an internal passageway and a sealing member across said passageway, said sealing member being arranged to permit passage of gas and to prevent passage of liquid;

and a plunger arranged in said barrel between said plug element and said first end, said plunger including a piston having an air channel therethrough, a plunger rod extending out of said first end and valve means for closing said air channel when said plunger rod is drawn in the direction of said first end.

2. A syringe assembly as specified in claim 1 wherein said sealing member has a selected thickness in the direction of air flow through said passageway and is arranged to seal only after liquid has penetrated said sealing member a distance which is less than said selected thickness whereby a small volume of said liquid is trapped in said sealing member.

3. A syringe assembly as specified in claim 2 wherein said sealing member comprises self-sealing porous polyethytene having a pore size selected to permit entry of liquid, and which seals said pores upon entry of said fluid.

4. A method for drawing a fixed maximum volume, air free blood sample comprising the steps of:

providing a syringe having a plug element at a fixed position in a syringe barrel, said plug element being air permeable and liquid impermeable and having a plunger arranged in said barrel on the side of said plug element away from the needle end of said syringe;

inserting the needle of said syringe into a blood vessel;

and drawing said plunger away from said plug thereby to draw air through said plug element until blood fills said syringe barrel between said needle and said plug element.

* * * * *